(12) United States Patent
Ksander et al.

(10) Patent No.: US 8,404,744 B2
(45) Date of Patent: *Mar. 26, 2013

(54) METHODS OF TREATMENT AND PHARMACEUTICAL COMPOSITION

(75) Inventors: Gary M Ksander, Milford, NJ (US); Randy L Webb, Flemington, NJ (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/328,769

(22) Filed: Dec. 16, 2011

(65) Prior Publication Data

US 2012/0138506 A1    Jun. 7, 2012

Related U.S. Application Data

(62) Division of application No. 12/147,570, filed on Jun. 27, 2008, now Pat. No. 8,101,659, which is a division of application No. 10/341,868, filed on Jan. 14, 2003, now Pat. No. 7,468,390.

(60) Provisional application No. 60/386,792, filed on Jun. 7, 2002, provisional application No. 60/349,660, filed on Jan. 17, 2002.

(51) Int. Cl.
*A61K 31/235* (2006.01)
*A61K 31/41* (2006.01)
*A61K 31/195* (2006.01)

(52) U.S. Cl. ......... 514/533; 514/381; 514/561; 514/563

(58) Field of Classification Search .................. 514/533, 514/381, 563
See application file for complete search history.

(56) References Cited

FOREIGN PATENT DOCUMENTS

| EP | 555175 | 1/1993 |
|---|---|---|
| EP | 0726072 | 2/1996 |

OTHER PUBLICATIONS

Lajemi et al., "Genetics of the renin-angiotensin-aldosterone system and risk of arterial disease"; ACE Inhibitors, Milestones in Drug Therapy, pp. 11-27; P. D'Orleans-Juste, G.E. Plante (2001).

Matsumoto et al.; "Blockade of renin-angiotensin system and enhancement of atrial natiuretic peptide with neutral endopeptidase inhibition cause natriuresis in congestive heart failure and renal dysfunction in conscious dogs", ASN Program and Abstracts, vol. 4, No. 3, p. 517 (Sep. 1993).

Robi et al., "Neutral endopeptidase inhibitors and combined inhibitors of neutral endopeptidase and angiotensin converting enzyme", Antihypersensitive Drugs, pp. 113-212, (1997).

Wohlfart, et al.; "Crosstalk between ACE Inhibitors, B2 kinin receptor and nitric oxide in endothelial cells", ACE Inhibitors, Milestones in Drug Therapy, P. D'Orleans-Juste, G.E. Piante (2001).

Trippodo et al., Repression of Angiotensin II and Potentiation of Bradykinin Contribute to the Synergistic Effects of Dual Metalloprotease Inhibition in Heart Failure:, J. Pharmacol. Exp. Ther., vol. 272, pp. 619-627, (1995).

Howes et al., "Angiotensin receptor antagonists and ACE inhibitors", Australian Family Physician, vol. 27, pp. 914-921, (1998).

Criscione et al., "Pharmacological profile of valsartan: a potent, orally active, nonpeptide antagonists of the angiotensin II AT-receptor sybtype", Br. J. Pharmacol., vol. 110, pp. 761-771, (1993).

Abstract of J. Pharmacol. Exp., Ther., vol. 265, pp. 1339-1347, (1993).

Search dated May 29, 2008 (26 pages) cited by opponent Mundipharma GMBH on Jun. 26, 2008, submitted in corresponding EP application 03704413.8.

Search dated May 29, 2008 (3 pages) cited by opponent Mundipharma GMBH on Jun. 26, 2008, submitted in corresponding EP application 03704413.8.

*Primary Examiner* — Jennifer M Kim
(74) *Attorney, Agent, or Firm* — Joseph T. Majka

(57) ABSTRACT

The invention relates a pharmaceutical composition comprising a combination of (i) the AT 1-antagonist valsartan or a pharmaceutically acceptable salt thereof and (ii) a NEP inhibitor or a pharmaceutically acceptable salt thereof and optionally a pharmaceutically acceptable carrier and to a method for the treatment or prevention of selected conditions or diseases.

10 Claims, No Drawings

METHODS OF TREATMENT AND PHARMACEUTICAL COMPOSITION

This application is a divisional application of Ser. No. 12/147,570, filed Jun. 27, 2008, which is a divisional application of Ser. No. 10/341,868, filed Jan. 14, 2003, now U.S. Pat. No. 7,468,390, which claims benefit of Provisional Application No. 60/386,792, filed Jun. 7, 2002 and Provisional Application No. 60/349,660, filed Jan. 17, 2002.

BACKGROUND OF THE INVENTION

The renin angiotensin system is a complex hormonal system comprised of a large molecular eight precursor, angiotensinogen, two processing enzymes, renin and angiotensin converting enzyme (ACE), and the vasoactive mediator angiotensin II (Ang II). See J. Cardiovasc. Pharmacol., 15(Supp B) (1990) p. S1-S5. The enzyme renin catalyzes the cleavage of angiotensinogen into the decapeptide angiotensin I, which has minimal biological activity on its own and is converted into the active octapeptide Ang II by ACE. Ang II has multiple biological actions on the cardiovascular system, including vasoconstriction, activation of the sympathetic nervous system, stimulation of aldosterone production, antinatriuresis, stimulation of vascular growth and stimulation of cardiac growth. Ang II functions as a pressor hormone and is involved the pathophysiology of several forms of hypertension.

The vasoconstrictive effects of angiotensin II are produced by its action on the non-striated smooth muscle cells, the stimulation of the formation of the adrenergenic hormones epinephrine and norepinephrine as well as the increase of the activity of the sympathetic nervous system as a result of the formation of norepinephrine. Angiotensin II also has an influence on electrolyte balance, produces e.g. antinatriuretic and antidiuretic effects in the kidney and thereby promotes the release of, on the one hand, the vasopressin peptide from the pituitary gland and, on the other hand, of aldosterone from the adrenal glomerulose. All these influences play an important part in the regulation of blood pressure, in increasing both circulating volume and peripheral resistance. Angiotensin II is also involved in cell growth and migration and in extracellular matrix formation.

Angiotensin II interacts with specific receptors on the surface of the target cell. It has been possible to identify receptor subtypes that are termed e.g. AT 1- and AT 2-receptors. In recent times great efforts have been made to identify substances that bind to the AT 1-receptor. Such active ingredients are often termed angiotensin II antagonists. Because of the inhibition of the AT 1-receptor such antagonists can be used e.g. as antihypertensives or for the treatment of congestive heart failure, among other indications. Angiotensin II antagonists are therefore understood to be those active ingredients which bind to the AT 1-receptor subtype.

Inhibitors of the renin angiotensin system are well known drugs that lower blood pressure and exert beneficial actions in hypertension and in congestive heart failure as described, for example, in N. Eng. J. Med. 316, 23 (1987) p. 1429-1435. A large number of peptide and non-peptide inhibitors of the renin angiotensin system are known, the most widely studied being the ACE inhibitors, which includes the drugs captopril, enalapril, lisinopril, benazepril and spirapril. Although a major mode of action of ACE inhibitors involves prevention of formation of the vasoconstrictor peptide Ang II, it has been reported in Hypertension, 16, 4 (1990) p. 363-370 that ACE cleaves a variety of peptide substrates, including the vasoactive peptides bradykinin and substance P. Prevention of the degradation of bradykinin by ACE inhibitors has been demonstrated, and the activity of the ACE inhibitors in some conditions has been reported in Circ. Res., 66, 1 (1990) p. 242-248 to be mediated by elevation of bradykinin levels rather than inhibition of Ang II formation. Consequently, it cannot be presumed that the effect of an ACE inhibitor is due solely to prevention of angiotensin formation and subsequent inhibition of the renin angiotensin system.

Neutral endopeptidase (EC 3.4.24.11; enkephalinase; atriopeptidase; NEP) is a zinc-containing metalloprotease that cleaves a variety of peptide substrates on the amino terminal side of aromatic amino acids. See Biochem. J., 241, (1987) p. 237-247. Substrates for this enzyme include, but are not limited to, atrial natriuretic factors (ANF, also known as ANP), brain natriuretic peptide (BNP), met and leu enkephalin, bradykinin, neurokinin A, and substance P.

ANPs are a family of vasodilator, diuretic and antihypertensive peptides which have been the subject of many recent reports in the literature, for example Annu. Rev. Pharm. Tox., 29, (1989) p. 23-54. One form, ANF 99-126, is a circulating peptide hormone which is released from the heart during conditions of cardiac distension. The function of ANF is to maintain salt and water homeostasis as well as to regulate blood pressure. ANF is rapidly inactivated in the circulation by at least two processes: a receptor-mediated clearance reported in Am. J. Physiol., 256 (1989) p. R469-R475 and an enzymatic inactivation via NEP reported in Biochem. J., 243 (1987) p. 183-187. It has been previously demonstrated that inhibitors of NEP potentiate the hypotensive, diuretic, natriuretic and plasma ANF responses to pharmacological injection of ANF in experimental animals. The potentiation of ANF by two specific NEP inhibitors is reported by Sybertz et al. in J. Pharmacol. Exp. Ther. 250, 2 (1989) p. 624-631 and in Hypertension, 15, 2 (1990) p. 152-161, while the potentiation of ANF by NEP in general was disclosed in U.S. Pat. No. 4,749,688. In U.S. Pat. No. 4,740,499 Olins disclosed the use of thiorphan and kelatorphan to potentiate atrial peptides. Moreover, NEP inhibitors lower blood pressure and exert ANF-like effects such as diuresis and increased cyclic guanosine 3',5'-monophosphate (cGMP) excretion in some forms of experimental hypertension. The antihypertensive action of NEP inhibitors is mediated through ANF because antibodies to ANF will neutralize the reduction in blood pressure.

Darrow et al. in European Patent Application 498361 disclose treating hypertension or congestive heart failure with a combination of certain angiotensin II antagonists or certain renin inhibitors with certain neutral endopeptidase inhibitors.

Powell et al. in European Patent Application 726072 disclose treating hypertension or congestive heart failure with a combination of the angiotensin II antagonist 2-butyl-6,7,8,9-tetrahydro-3-[[2'-(1H-tetrazol-5-yl)[1,1'-biphenyl]-4-yl]methyl]-1,3-diazaspiro[4.4]nonan-4-one with a neutral endopeptidase inhibitor or a dual acting vasopeptidase inhibitor (single molecular entity with both ACE and NEP inhibitory activities). Prolonged and uncontrolled hypertensive vascular disease ultimately leads to a variety of pathological changes in target organs such as the heart and kidney. Sustained hypertension can lead as well to an increased occurrence of stroke. Therefore, there is a strong need to evaluate the efficacy of antihypertensive therapy, an examination of additional cardiovascular endpoints, beyond those of blood pressure lowering, to get further insight into the benefits of combined treatment.

The nature of hypertensive vascular diseases is multifactorial. Under certain circumstances, drugs with different mechanisms of action have been combined. However, just considering any combination of drugs having different mode of action does not necessarily lead to combinations with advantageous effects. Accordingly, there is a need for more efficacious combination therapy which has less deleterious side effects.

Other objects, features, advantages and aspects of the present invention will become apparent to those of skill from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

DETAILED DESCRIPTION OF THE PREFERRED EMBODIMENTS

In one aspect the present invention relates to pharmaceutical combinations comprising valsartan or pharmaceutically acceptable salts thereof and a neutral endopeptidase (NEP) inhibitor or a pharmaceutically effective salts thereof, optionally in the presence of a pharmaceutically acceptable carrier and pharmaceutical compositions comprising them.

In another embodiment the present invention relates to methods of treating cardiac and renal related conditions by administration of the pharmaceutical composition comprising valsartan plus a NEP inhibitor.

Valsartan is the AT 1 receptor antagonist (S)—N-(1-carboxy-2-methyl-prop-1-yl)-N-pentanoyl-N-[2; (1H-tetrazol-5-yl)biphenyl-4-yl-methyl]amine of formula (I) and is disclosed in EP 0443983 A and U.S. Pat. No. 5,399,578, the

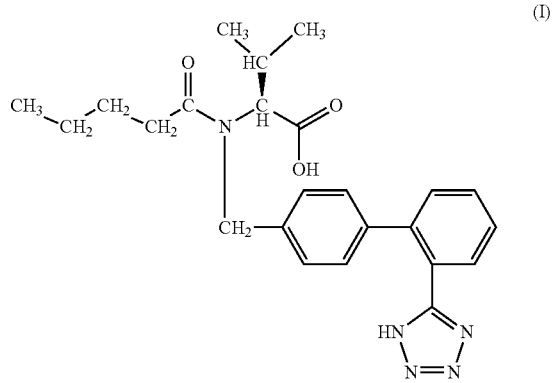 [SMILES: CCCCC(=O)N(Cc1ccc(-c2ccccc2-c2nnn[nH]2)cc1)[C@H](C(=O)O)C(C)C]

disclosures of which are incorporated herein in their entirety as if set forth herein.

A NEP inhibitor useful in said combination is a compound of the formula (II)

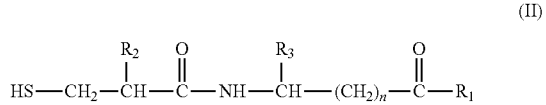

and pharmaceutically acceptable salts thereof wherein:

$R_2$ is alkyl of 1 to 7 carbons, trifluoromethyl, phenyl, substituted phenyl, —$(CH_2)_{1\ to\ 4}$-phenyl, or —$(CH_2)_{1\ to\ 4}$-substituted phenyl;

$R_3$ is hydrogen, alkyl of 1 to 7 carbons, phenyl, substituted phenyl, —$(CH_2)_{1\ to\ 4}$-phenyl, or —$(CH_2)_{1\ to\ 4}$-substituted phenyl;

$R_1$ is hydroxy, alkoxy of 1 to 7 carbons, or $NH_2$;

n is an integer from 1 to 15; and the term substituted phenyl refers to a substituent selected from lower alkyl of 1 to 4 carbons, lower alkoxy of 1 to 4 carbons, lower alkylthio of 1 to 4 carbons, hydroxy, Cl, Br, or F.

Preferred selective neutral endopeptidase inhibitors of formula II include compounds wherein:

$R_2$ is benzyl;

$R_3$ is hydrogen;

n is an integer from 1 to 9; and $R_1$ is hydroxy.

Even more preferred selective neutral endopeptidase inhibitors of formula II are reported in the literature as SQ 28,603 which is the compound of formula II wherein:

$R_2$ is benzyl;

$R_3$ is hydrogen;

n is one; and $R_1$ is hydroxy.

The preparation of the selective neutral endopeptidase inhibitors of formula II wherein $R_2$ is other than trifluoromethyl are disclosed by Delaney et al. in U.S. Pat. No. 4,722,810. The preparation of the selective neutral endopeptidase inhibitors of formula II wherein $R_2$ is trifluoromethyl are disclosed by Delaney et al in U.S. Pat. No. 5,223,516.

NEP inhibitors within the scope of the present invention include compounds disclosed in U.S. Pat. No. 4,610,816, herein incorporated by reference, including in particular N—[N-[1(S)-carboxyl-3-phenylpropyl]-(S)-phenylalanyl]-(S)-isoserine and N—[N-[((1S)-carboxy-2-phenypethyl]-(S)-phenylalanyl]-☐-alanine; compounds disclosed in U.S. Pat. No. 4,929,641, in particular N-[2(S)-mercaptomethyl-3-(2-methylphenyl)-propionyl]methionine; SQ 28603 (N-[2-(mercaptonmethyl)-1-oxo-3-phenylpropyl]-☐-alanine), disclosed in South African Patent Application 84/0670; UK 69578 (cis-4-[[[1-[2-carboxy-3-(2-methoxyethoxy)propyl]-cyclopentyl]carbonyl]amino]-cyclohexanecarboxylic acid) and its active enantiomer(s); thiorphan and its enantiomers; retro-thiorphan; phosphoramidon; and SQ 29072 (7-[[2-(mercaptomethyl)-1-oxo-3-phenylpropyl]amino]-heptanoic acid). Also suitable for use are any pro-drug forms of the above-listed NEP inhibitors, e.g., compounds in which one or more carboxylic acid groups are esterified.

NEP inhibitors within the scope of the present invention also include the compounds disclosed in U.S. Pat. No. 5,217,996, particularly, N-(3-carboxy-1-oxopropyl)-(4S)-p-phenylphenylmethyl)-4-amino-2R-methylbutanoic acid ethyl ester; the compounds disclosed in EP 00342850, particularly (S)-cis-4-[1-[2-(5-indanyloxycarbonyl)-3-(2-methoxyethoxy)propyl]-1-cyclopentanecarboxamido]-1-cyclohexanecarboxylic acid; the compounds disclosed in GB 02218983, particularly 3-(1-[6-endo-hydroxymethylbicyclo[2,2,1]heptane-2-exo-carbamoyl]cyclopentyl)-2-(2-methoxyethyl)propanoic acid; the compounds disclosed in WO 92/14706, particularly N-(1-(3-(N-t-butoxycarbonyl-(S)-prolylamino)-2 (S)-t-butoxy-carbonylpropyl)cyclopentanecarbonyl)-O-benzyl-(S)-serine methyl ester; the compounds disclosed in EP 00343911; the compounds disclosed in JP 06234754; the compounds disclosed in EP 00361365, particularly 4-[[2-(Mercaptomethyl)-1-oxo-3-phenylpropyl]amino]benzoic acid; the compounds disclosed in WO 90/09374, particularly 3-[1-(Cis-4-carboxycarbonyl-cis-3-butylcyclohexyl-r-1-carboamoyl)cyclopentyl]-2S-(2-methoxyethoxymethyl)propanoic acid; the compounds disclosed in JP 07157459, particularly N-((2S)-2-(4-biphenylmethyl)-4-carboxy-5-phenoxyvaleryl)glycine; the compounds disclosed in WO 94/15908 particularly N-(1-(N-hydroxycarbamoylmethyl)-1-cyclopentanecarbonyl)-L-phenylalanine; the compounds disclosed in U.S. Pat. No. 5,273,990 particularly (S)-(2-biphenyl-4-yl)-1-(1H-tetrazol-5-yl)ethylamino) methylphosphonic acid; the compounds disclosed in U.S. Pat. No. 5,294,632 particularly (S)-5-(N-(2-(phosphonomethylamino)-3-(4-biphenyl)propionyl)-2-aminoethyl)tetrazole; the compounds disclosed in U.S. Pat. No. 5,250,522, particularly □-Alanine, 3-[1,1'-biphenyl]-4-yl-N-[diphenoxyphosphinyl)methyl]-L-alanyl; the compounds disclosed in EP 00636621, particularly N-(2-carboxy-4-thienyl)-3-mercapto-2-benzylpropanamide; the compounds disclosed in WO 93/09101, particularly 2-(2-mercaptomethyl-3-phenyl-propionamido)thiazol-4-ylcarboxylic acid; the compounds disclosed in EP 00590442 particularly ((L)-(1-((2,2-dimethyl-1,3-dioxolan-4-yl)-methoxy)carbonyl)-2-phenyl-ethyl)-L-phenylalanyl)-□-alanine, N—[N-[(L)-[1-[(2,2-dimethyl-1,3-dioxolan-4-yl)-methoxy]carbonyl]-2-phenylethyl]-L-phenylalanyl]-(R)-alanine, N—[N-[(L)-1-carboxy-2-phenylethyl]-L-phenylalanyl]-(R)-alanine, N-[2-acetylthiomethyl-3-(2-methyl-phenyl)propionyl]-methionine ethyl ester, N-[2-mercaptomethyl-3-(2-methylphenyl)propioyl]-methionine, N-[2(S)-mercaptomethyl-3-(2-methylphenyl)propanoyl]-(S)-isoserine, N—(S)-[3-mercapto-2-(2-methylphenyl) propionyl]-(S)-2-methoxy-(R)-alanine, N-[1-[[1(S)-benzyloxycarbonyl-3-phenylpropyl]amino] cyclopentylcarbonyl]-(S)-isoserine, N-[1-[[1(S)-carbonyl-3-phenylpropyl]amino]-cyclopentylcarbonyl]-(S)-isoserine, 1,1'-[dithiobis-[2(S)-(2-methylbenzyl)-1-oxo-3,1-propanediyl]]-bis-(S)-isoserine, 1,1'-[dithiobis-[2(S)-(2-methylbenzyl)-1-oxo-3,1-propanediyl]]-bis-(S)-methionine, N-(3-phenyl-2-(mercaptomethyl)-propionyl)-(S)-4-(methylmercapto)methionine, N-[2-acetylthiomethyl-3-phenyl-propionyl]-3-aminobenzoic acid, N-[2-mercaptomethyl-3-phenyl-propionyl]-3-aminobenzoic acid, N-[1-(2-carboxy-4-phenylbutyl)-cyclopentanecarbonyl]-(S)-isoserine, N-[1-(acetylthiomethyl)cyclopentane-carbonyl]-(S)-methionine ethyl ester, 3(S)-[2-(acetylthiomethyl)-3-phenyl-propionyl] amino-ε-caprolactam; and the compounds disclosed in WO 93/10773 particularly N-(2-acetylthiomethyl-3-(2-methylphenyl)propionyl)-methionine ethyl ester.

The compounds to be combined can be present as pharmaceutically acceptable salts. If these compounds have, for example, at least one basic center, they can form acid addition salts. Corresponding acid addition salts can also be formed having, if desired, an additionally present basic center. The compounds having at least one acid group (for example COOH) can also form salts with bases. Corresponding internal salts may furthermore be formed, if a compound comprises e.g. both a carboxy and an amino group.

With respect to N-(3-carboxy-1-oxopropyl)-(4S)-p-phenylphenylmethyl)-4-amino-2R-methylbutanoic acid ethyl ester, preferred salts include the sodium salt disclosed in U.S. Pat. No. 5,217,996, the triethanolamine salt and the tris(hydroxymethyl)aminomethane salt. Preparation of the triethanolamine salt and the tris(hydroxymethyl)aminomethane salt may be carried out as follows: Triethanolamine—To N-(3-carboxy-1-oxopropyl)-(4S)-p-phenylphenylmethyl)-4-amino-2R-methylbutanoic acid ethyl ester (349 mg, 0.848 mmol) is added 5 ml of ethyl ether and 0.113 ml (0.848 mmol) of triethanolamine in 1 ml of ethyl acetate. The solid was collected and dried melting at 69-71° C.

Tris(hydroxymethyl)aminomethane—To N-(3-carboxy-1-oxopropyl)-(4S)-p-phenylphenylmethyl)-4-amino-2R-methylbutanoic acid ethyl ester (3.2 g (7.78 mmol) is added 32 ml of ethyl acetate and 940 mg (7.78 mmol) tris(hydroxymethyl)aminomethane. The suspension is diluted with 45 ml of ethyl acetate and refluxed overnight (~20 hr). The reaction is cooled to 0° C., filtered, solid washed with ethyl acetate and dried melting at 114-115° C.

It has surprisingly been found that, a combination of valsartan and a NEP inhibitor achieves greater therapeutic effect than the administration of valsartan, ACE inhibitors or NEP inhibitors alone and promotes less angioedema than is seen with the administration of a vasopeptidase inhibitor alone. Greater efficacy can also be documented as a prolonged duration of action. The duration of action can be monitored as either the time to return to baseline prior to the next dose or as the area under the curve (AUC) and is expressed as the product of the change in blood pressure in millimeters of mercury (change in mmHg) and the duration of the effect (minutes, hours or days).

Further benefits are that lower doses of the individual drugs to be combined according to the present invention can be used to reduce the dosage, for example, that the dosages need not only often be smaller but are also applied less frequently, or can be used to diminish the incidence of side effects. The combined administration of valsartan or a pharmaceutically acceptable salt thereof and a NEP inhibitor or a pharmaceutically acceptable salt thereof results in a significant response in a greater percentage of treated patients, that is, a greater responder rate results, regardless of the underlying etiology of the condition. This is in accordance with the desires and requirements of the patients to be treated.

It can be shown that combination therapy with valsartan and a NEP inhibitor results in a more effective antihypertensive therapy (whether for malignant, essential, reno-vascular, diabetic, isolated systolic, or other secondary type of hypertension) through improved efficacy as well as a greater responder rate. The combination is also useful in the treatment or prevention of heart failure such as (acute and chronic) congestive heart failure, left ventricular dysfunction and hypertrophic cardiomyopathy, diabetic cardiac myopathy, supraventricular and ventricular arrhythmias, atrial fibrillation, atrial flutter or detrimental vascular remodeling. It can further be shown that a valsartan and NEP inhibitor therapy proves to be beneficial in the treatment and prevention of myocardial infarction and its sequelae. A valsartan plus NEP inhibitor combination is also useful in treating atherosclerosis, angina (whether stable or unstable), and renal insufficiency (diabetic and non-diabetic). Furthermore, combination therapy using valsartan and a NEP inhibitor can improve endothelial dysfunction, thereby providing benefit in diseases in which normal endothelial function is disrupted such as heart failure, angina pectoris and diabetes. Furthermore, the combination of the present invention may be used for the treatment or prevention of secondary aldosteronism, primary and secondary pulmonary hypertension, renal failure conditions, such as diabetic nephropathy, glomerulonephritis, scleroderma, glomerular sclerosis, proteinuria of primary renal disease, and also renal vascular hypertension, diabetic retinopathy, the management of other vascular disorders, such as migraine, peripheral vascular disease, Raynaud's disease, luminal hyperplasia, cognitive dysfunction (such as Alzheimer's), glaucoma and stroke.

The person skilled in the pertinent art is fully enabled to select a relevant test model to prove the efficacy of a combination of the present invention in the hereinbefore and hereinafter indicated therapeutic indications.

Representative studies are carried out with a combination of valsartan and N-(3-carboxy-1-oxopropyl)-(4S)-p-phenylphenylmethyl)-4-amino-2R-methylbutanoic acid ethyl ester, e.g. applying the following methodology:

Drug efficacy is assessed in various animal models including the deoxycorticosterone acetate—salt rat (DOCA-salt) and the spontaneously hypertensive rat (SHR), either maintained on a normal salt diet or with salt loading (4-8% salt in rat chow or 1% NaCl as drinking water).

The DOCA-salt test model utilizes either an acute or chronic study protocol. An acute study procedure involves assessment of the effects of various test substances over a six-hour experimental period using rats with indwelling femoral arterial and venous catheters. The Acute Study Procedure evaluates test substances for their ability to reduce blood pressure during the established phase of DOCA-salt hypertension. In contrast, the Chronic Study Procedure assesses the ability of test substances to prevent or delay the rise in blood pressure during the development phase of DOCA-salt hypertension. Therefore, blood pressure will be monitored in the chronic study procedure by means of a radiotransmitter. The radiotransmitter is surgically implanted into the abdominal aorta of rats, prior to the initiation of DOCA-salt treatment and thus, prior to the induction of hypertension. Blood pressure is chronically monitored for periods of up 6 weeks (approximately one week prior to DOCA-salt administration and for 5 weeks thereafter).

Rats are anesthetized with 2-3% isoflurane in oxygen inhalant followed by Amytal sodium (amobarbital) 100 mg/kg, ip. The level of anesthesia is assessed by a steady rhythmic breathing pattern.

Acute Study Procedure:

Rats undergo a unilateral nephrectomy at the time of DOCA implantation. Hair is clipped on the left flank and the back of the neck and scrubbed with sterile alcohol swabs and povidone/iodine. During surgery rats are placed on a heating pad to maintain body temperature at 37 degrees C.

A 20 mm incision is made through the skin and underlying muscle to expose the left kidney. The kidney is freed of surrounding tissue, exteriorized and two ligatures (3-0 silk) are tied securely around the renal artery and vein proximal to their juncture with the aorta. The renal artery and vein are then severed and the kidney removed. The muscle and skin wounds are closed with 4-0 silk suture and stainless steel wound clips, respectively. At the same time, a 15 mm incision is made on the back of the neck and a 3-week-release pellet (Innovative Research of America, Sarasota, Fla.) containing deoxycorticosterone acetate (100 mg/kg) is implanted subcutaneously. The wound is then closed with stainless-steel clips and both wounds are treated with povidone/iodine; the rats are given a post-surgical intramuscular injection of procaine penicillin G (100,000 U) and buprenorphine (0.05-0.1 mg/kg) s.c. The rats are immediately placed on 1% NaCl+0.2% KCl drinking water; this treatment continues for at least 3 weeks at which time the animals have become hypertensive and available for experimentation.

Forty-eight hours prior to experimentation, animals are anesthetized with isoflurane and catheters are implanted in the femoral artery and vein for measuring arterial pressure, collection of blood, and administration of test compounds. Rats are allowed to recover for 48 hours while tethered in a Plexiglas home cage, which also serves as the experimental chamber.

Chronic Study Procedure:

This procedure is the same as above except that rats are implanted with a radiotransmitter, 7-10 days prior to the unilateral nephrectomy and initiation of DOCA and salt. In addition, rats do not undergo surgery for placement of femoral arterial and venous catheters. Radiotransmitters are implanted as described in M. K. Bazil, C. Krulan and R. L. Webb. Telemetric monitoring of cardiovascular parameters in conscious spontaneously hypertensive rats. J. Cardiovasc. Pharmacol. 22: 897-905, 1993.

Protocols are then set-up on the computer for measurement of blood pressure, heart rate, etc, at predetermined time points. Baseline data is collected at various time points and over various time intervals. For example, baseline or pre-dose values usually consist of data collection and averaging over 3 consecutive, 24-hour time periods prior to drug administration.

Blood pressure, heart rate and activity are determined at various pre-selected time points before, during, and after drug administration. All measurements are performed in unrestrained and undisturbed animals. The maximum study time, determined by battery life, could be as long as nine months. For studies of this duration, rats are dosed orally (1-3 ml/kg vehicle), no more than twice daily or drug is administered via the drinking water or mixed with food. For studies of a shorter duration, that is, up to 8 weeks, drugs are given via subcutaneously implanted osmotic minipumps. Osmotic minipumps are selected based on drug delivery rate and time. Valsartan dosages range from 1 to 10 mg/kg/day and N-(3-carboxy-1-oxopropyl)-(4S)-p-phenylphenylmethyl)-4-amino-2R-methylbutanoic acid ethyl ester range from 10 to 50 mg/kg/day.

Additionally, SHR are utilized to study the effects of valsartan in combination with N-(3-carboxy-1-oxopropyl)-(4S)-p-phenylphenylmethyl)-4-amino-2R-methylbutanoic acid ethyl ester. The hypertensive background of the SHR is modified either by chronic salt loading in an effort to suppress the renin angiotensin system (RAS) or chronic salt depletion to activate the RAS in the SHR. These manipulations will be carried out to more extensively evaluate the efficacy of the various test substances. Experiments performed in spontaneously hypertensive rats (SHR) are supplied by Taconic Farms, Germantown, N.Y. (Tac:N(SHR)fBR). A radiotelemetric device (Data Sciences International, Inc., St. Paul, Minn.) is implanted into the lower abdominal aorta of all test animals between the ages of 14 to 16 weeks of age. All SHR are allowed to recover from the surgical implantation procedure for at least 2 weeks prior to the initiation of the experiments. Cardiovascular parameters are continuously monitored via the radiotransmitter and transmitted to a receiver where the digitized signal is then collected and stored using a computerized data acquisition system. Blood pressure (mean arterial, systolic and diastolic pressure) and heart rate are monitored in conscious, freely moving and undisturbed SHR in their home cages. The arterial blood pressure and heart rate are measured every 10 minutes for 10 seconds and recorded. Data reported for each rat represent the mean values averaged over a 24 hour period and are made up of the 144-10 minute samples collected each day. The baseline values for blood pressure and heart rate consist of the average of three consecutive 24 hour readings taken prior to initiating the drug treatments. All rats are individually housed in a temperature and humidity controlled room and are maintained on a 12 hour light dark cycle.

In addition to the cardiovascular parameters, weekly determinations of body weight also are recorded in all rats. Treatments are administered in the drinking water, via daily oral gavage or in osmotic minipumps as stated above. If given in drinking water, water consumption is measured five times per week. Valsartan and N-(3-carboxy-1-oxopropyl)-(4S)-p-phenylphenylmethyl)-4-amino-2R-methylbutanoic acid ethyl ester doses for individual rats are then calculated based on water consumption for each rat, the concentration of drug substance in the drinking water, and individual body weights. All drug solutions in the drinking water are made up fresh every three to four days. Typical dosages for valsartan in drinking water range from 3 to 30 mg/kg/day whereas the dosage of N-(3-carboxy-1-oxopropyl)-(4S)-p-phenylphenylmethyl)-4-amino-2R-methylbutanoic acid ethyl ester is highly dependent upon the specific agent used. In most situations, a daily dose will not exceed 50 mg/kg/day when administered as the monotherapy. In combination, lower dosages of each agent are used and correspondingly, valsartan is given in the range of 1 to 30 mg/kg/day and N-(3-carboxy-1-oxopropyl)-(4S)-p-phenylphenylmethyl)-4-amino-2R-methylbutanoic acid ethyl ester in dosages below 50 mg/kg/day. However, in cases wherein the responder rate is increased with combination treatment, the dosages are identical to those used as monotherapy.

When drugs are administered by oral gavage, the dose of valsartan ranges from 1 to 50 mg/kg/day and N-(3-carboxy-1-oxopropyl)-(4S)-p-phenylphenylmethyl)-4-amino-2R-methylbutanoic acid ethyl ester does not exceed 100 mg/kg/day.

Upon completion of the chronic studies, SHR or DOCA-salt rats are anesthetized and the heart rapidly removed. After separation and removal of the atrial appendages, left ventricle and left plus right ventricle (total) are weighed and recorded. Left ventricular and total ventricular mass are then normalized to body weight and reported. All values reported for blood pressure and cardiac mass represent the group mean±sem.

Vascular function and structure are evaluated after treatment to assess the beneficial effects of the combination. SHR are studied according to the methods described by Intengan H D, Thibault G, Li J S, Schiffrin E L, Circulation 1999, 100 (22): 2267-2275. Similarly, the methodology for assessing vascular function in DOCA-salt rats is described in Intengan H D, Park J B, Schiffrin, E L, Hypertension, 1999, 34(4 Part 2): 907-913.

The available results indicate an unexpected therapeutic effect of a combination according to the invention.

In one aspect is the object of this invention to provide a pharmaceutical combination composition, e.g. for the treatment or prevention of a condition or disease selected from the group consisting of hypertension, heart failure such as (acute and chronic) congestive heart failure, left ventricular dysfunction and hypertrophic cardiomyopathy, diabetic cardiac myopathy, supraventricular and ventricular arrhythmias, atrial fibrillation, atrial flutter, detrimental vascular remodeling, myocardial infarction and its sequelae, atherosclerosis, angina (whether unstable or stable), renal insufficiency (diabetic and non-diabetic), heart failure, angina pectoris, diabetes, secondary aldosteronism, primary and secondary pulmonary hypertension, renal failure conditions, such as diabetic nephropathy, glomerulonephritis, scleroderma, glomerular sclerosis, proteinuria of primary renal disease, and also renal vascular hypertension, diabetic retinopathy, the management of other vascular disorders, such as migraine, peripheral vascular disease, Raynaud's disease, luminal hyperplasia, cognitive dysfunction (such as Alzheimer's), glaucoma and stroke which composition comprises (i) the AT 1-antagonists valsartan or a pharmaceutically acceptable salt thereof and (ii) a NEP inhibitor or a pharmaceutically acceptable salt thereof and a pharmaceutically acceptable carrierthis composition, components (i) and (ii) can be obtained and administered together, one after the other or separately in one combined unit dose form or in two separate unit dose forms. The unit dose form may also be a fixed combination.

A further aspect of the present invention is a method for the treatment or prevention of a condition or disease selected from the group consisting of hypertension, heart failure such as (acute and chronic) congestive heart failure, left ventricular dysfunction and hypertrophic cardiomyopathy, diabetic cardiac myopathy, supraventricular and ventricular arrhythmias, atrial fibrillation, atrial flutter, detrimental vascular remodeling, myocardial infarction and its sequelae, atherosclerosis, angina (whether unstable or stable), renal insufficiency (diabetic and non-diabetic), heart failure, angina pectoris, diabetes, secondary aldosteronism, primary and secondary pulmonary hypertension, renal failure conditions, such as diabetic nephropathy, glomerulonephritis, scleroderma, glomerular sclerosis, proteinuria of primary renal disease, and also renal vascular hypertension, diabetic retinopathy, the management of other vascular disorders, such as migraine, peripheral vascular disease, Raynaud's disease, luminal hyperplasia, cognitive dysfunction (such as Alzheimer's), glaucoma and stroke, comprising administering a therapeutically effective amount of combination of (i) the AT 1-antagonists valsartan or a pharmaceutically acceptable salt thereof and (ii) a NEP inhibitor or a pharmaceutically acceptable salt thereof and a pharmaceutically acceptable carrier to a mammal in need of such treatment.

A therapeutically effective amount of each of the component of the combination of the present invention may be administered simultaneously or sequentially and in any order.

The corresponding active ingredient or a pharmaceutically acceptable salt thereof may also be used in form of a hydrate or include other solvents used for crystallization.

The pharmaceutical compositions according to the invention can be prepared in a manner known per se and are those suitable for enteral, such as oral or rectal, and parenteral administration to mammals (warm-blooded animals), including man, comprising a therapeutically effective amount of the pharmacologically active compound, alone or in combination with one or more pharmaceutically acceptable carriers, especially suitable for enteral or parenteral application. Typical oral formulations include tablets, capsules, syrups, elixirs and suspensions. Typical injectable formulations include solutions and suspensions.

The typical pharmaceutically acceptable carriers for use in the formulations described above are exemplified by: sugars such as lactose, sucrose, mannitol and sorbitol; starches such as cornstarch, tapioca starch and potato starch; cellulose and derivatives such as sodium carboxymethyl cellulose, ethyl cellulose and methyl cellulose; calcium phosphates such as dicalcium phosphate and tricalcium phosphate; sodium sulfate; calcium sulfate; polyvinylpyrrolidone; polyvinyl alcohol; stearic acid; alkaline earth metal stearates such as magnesium stearate and calcium stearate; stearic acid; vegetable oils such as peanut oil, cottonseed oil, sesame oil, olive oil and corn oil; non-ionic, cationic and anionic surfactants; ethylene glycol polymers; betacyclodextrin; fatty alcohols; and hydrolyzed cereal solids, as well as other non-toxic compatible fillers, binders, disintegrants, buffers, preservatives, antioxidants, lubricants, flavoring agents, and the like commonly used in pharmaceutical formulations.

The invention also relates to combining separate pharmaceutical compositions in kit form. That is a kit combining two separate units: a valsartah pharmaceutical composition and a NEP inhibitor pharmaceutical composition. The kit form is particularly advantageous when the separate components must be administered in different dosage forms (e.g. parenteral valsartan formulation and oral NEP formulation) or are administered at different dosage intervals.

These pharmaceutical preparations are for enteral, such as oral, and also rectal or parenteral, administration to homeotherms, with the preparations comprising the pharmacological active compound either alone or together with customary pharmaceutical auxiliary substances. For example, the pharmaceutical preparations consist of from about 0.1% to 90%, preferably of from about 1% to about 80%, of the active compounds. Pharmaceutical preparations for enteral or parenteral administration are, for example, in unit dose forms, such as coated tablets, tablets, capsules or suppositories and also ampoules. These are prepared in a manner which is known per se, for example using conventional mixing, granulation, coating, solubulizing or lyophilizing processes. Thus, pharmaceutical preparations for oral use can be obtained by combining the active compounds with solid excipients, if desired granulating a mixture which has been obtained, and, if required or necessary, processing the mixture or granulate into tablets or coated tablet cores after having added suitable auxiliary substances.

The dosage of the active compound can depend on a variety of factors, such as mode of administration, homeothermic species, age and/or individual condition.

Preferred dosages for the active ingredients of the pharmaceutical combination according to the present invention are therapeutically effective dosages, especially those which are commercially available.

Normally, in the case of oral administration, an approximate daily dose of from about 1 mg to about 360 mg is to be estimated e.g. for a patient of approximately 75 kg in weight.

Valsartan is supplied in the form of suitable dosage unit form, for example, a capsule or tablet, and comprising a therapeutically effective amount, e.g. from about 20 to about 320 mg, of valsartan which may be applied to patients. The application of the active ingredient may occur up to three times a day, starting e.g. with a daily dose of 20 mg or 40 mg of valsartan, increasing via 80 mg daily and further to 160 mg daily up to 320 mg daily. Preferably, valsartan is applied once a day or twice a day in heart failure patients with a dose of 80 mg or 160 mg, respectively, each. Corresponding doses may be taken, for example, in the morning, at mid-day or in the evening. Preferred is q.d. or b.i.d. administration in heart failure.

In case of NEP inhibitors, preferred dosage unit forms are, for example, tablets or capsules comprising e.g. from about 20 mg to about 800 mg, preferably from about 50 mg to about 700 mg, even more preferably from about 100 mg to about 600 mg and even more preferably from about 100 mg to about 300 mg, administered once a day. The above doses encompass a therapeutically effective amount of the active ingredients of the present invention.

The following examples illustrate the above-described invention; however, it is not intended to restrict the scope of this invention in any manner.

Formulation Example 1

Film-Coated Tablets

| Components | Composition Per Unit (mg) | Standards |
|---|---|---|
| Granulation | | |
| Valsartan [=active ingredient] | 80.00 | |
| Microcrystalline cellulose/ Avicel PH 102 | 54.00 | NF, Ph. Eur |
| Crospovidone | 20.00 | NF, Ph. Eur |
| Colloidal anhydrous silica/ colloidal silicon dioxide/Aerosil 200 | 0.75 | Ph. Eur/ NF |
| Magnesium stearate | 2.5 | NF, Ph. Eur |
| Blending | | |
| Colloidal anhydrous silica/ colloidal silicon dioxide/Aerosil 200 | 0.75 | Ph. Eur/ NF |
| Magnesium stearate | 2.00 | NF, Ph. Eur |
| Coating | | |
| Purified water*) | — | |
| DIOLACK pale red 00F34899 | 7.00 | |
| Total tablet mass | 167.00 | |

*)Removed during processing.

The film-coated tablet is manufactured e.g. as follows:

A mixture of valsartan, microcrystalline cellulose, crospovidone, part of the colloidal anhydrous silica/colloidal silicon dioxide/Aerosile 200, silicon dioxide and magnesium stearate is premixed in a diffusion mixer and then sieve through a screening mill. The resulting mixture is again premixed in a diffusion mixer, compacted in a roller compactor and then sieve through a screening mill. To the resulting mixture, the rest of the colloidal anhydrous silica/colloidal silicon dioxide/Aerosile 200 are added and the final blend is made in a diffusion mixer. The whole mixture is compressed in a rotary tabletting machine and the tablets are coated with a film by using Diolack pale red in a perforated pan.

Formulation Example 2

Film-Coated Tablets

| Components | Composition Per Unit (mg) | Standards |
|---|---|---|
| Granulation | | |
| Valsartan [=active ingredient] | 160.00 | |
| Microcrystalline cellulose/ Avicel PH 102 | 108.00 | NF, Ph. Eur |
| Crospovidone | 40.00 | NF, Ph. Eur |
| Colloidal anhydrous silica/ colloidal silicon dioxide/Aerosil 200 | 1.50 | Ph. Eur/ NF |
| Magnesium stearate | 5.00 | NF, Ph. Eur |
| Blending | | |
| Colloidal anhydrous silica/ colloidal silicon dioxide/Aerosil 200 | 1.50 | Ph. Eur/ NF |
| Magnesium stearate | 4.00 | NF, Ph. Eur |
| Coating | | |
| Opadry Light Brown 00F33172 | 10.00 | |
| Total tablet mass | 330.00 | |

The film-coated tablet is manufactured e.g. as described in Formulation Example 1.

Formulation Example 3

Film-Coated Tablets

| Components | Composition Per Unit (mg) | Standards |
|---|---|---|
| Core: Internal phase | | |
| Valsartan [=active ingredient] | 40.00 | |
| Silica, colloidal anhydrous (Colloidal silicon dioxide) [=Glidant] | 1.00 | Ph. Eur, USP/NF |
| Magnesium stearate [=Lubricant] | 2.00 | USP/NF |
| Crospovidone [Disintegrant] | 20.00 | Ph. Eur |
| Microcrystalline cellulose [=Binding agent] | 124.00 | USP/NF |
| External phase | | |
| Silica, colloidal anhydrous, (Colloidal silicon dioxide) [=Glidant] | 1.00 | Ph. Eur, USP/NF |
| Magnesium stearate [Lubricant] | 2.00 | USP/NF |
| Film coating | | |
| Opadry ® brown OOF 16711*) | 9.40 | |
| Purified Water**) | — | |
| Total tablet mass | 199.44 | |

*)The composition of the Opadry ® brown OOF16711 coloring agent is tabulated below.
**)Removed during processing Opadry® Composition:

| Ingredient | Approximate % Composition |
|---|---|
| Iron oxide, black (C.I. No. 77499, E 172) | 0.50 |
| Iron oxide, brown (C.I. No. 77499, E 172 | 0.50 |
| Iron oxide, red (C.I. No. 77491, E 172) | 0.50 |
| Iron oxide, yellow (C.I. No. 77492, E 172) | 0.50 |
| Macrogolum (Ph. Eur) | 4.00 |
| Titanium dioxide (C.I. No. 77891, E 171) | 14.00 |
| Hypromellose (Ph. Eur) | 80.00 |

The film-coated tablet is manufactured e.g. as described in Formulation Example 1.

Formulation Example 4

Capsules

| Components | Composition Per Unit (mg) |
|---|---|
| Valsartan [=active ingredient] | 80.00 |
| Microcrystalline cellulose | 25.10 |
| Crospovidone | 13.00 |
| Povidone | 12.50 |
| Magnesium stearate | 1.30 |
| Sodium lauryl sulphate | 0.60 |
| Shell | |
| Iron oxide, red (C.I. No. 77491, EC No. E 172) | 0.123 |
| Iron oxide, yellow (C.I. No. 77492, EC No. E 172) | 0.123 |
| Iron oxide, black (C.I. No. 77499, EC No. E 172) | 0.245 |
| Titanium dioxide | 1.540 |
| Gelatin | 74.969 |
| Total tablet mass | 209.50 |

The tablet is manufactured e.g. as follows:

Granulation/Drying

Valsartan and microcrystallin cellulose are spray-granulated in a fluidized bed granulator with a granulating solution consisting of povidone and sodium lauryl sulphate dissolved in purified water. The granulate obtained is dried in a fluidized bed dryer.

Milling/Blending

The dried granulate is milled together with crospovidone and magnesium stearate. The mass is then blended in a conical screw type mixer for approximately 10 minutes.

Encapsulation

The empty hard gelatin capsules are filled with the blended bulk granules under controlled temperature and humidity conditions. The filed capsules are dedusted, visually inspected, weight checked and quarantined until by Quality assurance department.

Formulation Example 5

Capsules

| Components | Composition Per Unit (mg) |
|---|---|
| Valsartan [= active ingredient] | 160.00 |
| Microcrystalline cellulose | 50.20 |
| Crospovidone | 26.00 |
| Povidone | 25.00 |
| Magnesium stearate | 2.60 |
| Sodium lauryl sulphate | 1.20 |
| Shell | |
| Iron oxide, red (C.I. No. 77491, EC No. E 172) | 0.123 |
| Iron oxide, yellow (C.I. No. 77492, EC No. E 172) | 0.123 |
| Iron oxide, black (C.I. No. 77499, EC No. E 172) | 0.245 |
| Titanium dioxide | 1.540 |
| Gelatin | 74.969 |
| Total tablet mass | 342.00 |

The formulation is manufactured e.g. as described in Formulation Example 4.

Formulation Example 6

Hard Gelatine Capsule

| Components | Composition Per Unit (mg) |
|---|---|
| Valsartan [=active ingredient] | 80.00 |
| Sodium laurylsulphate | 0.60 |
| Magnesium stearate | 1.30 |
| Povidone | 12.50 |
| Crospovidone | 13.00 |
| Microcrystalline cellulose | 21.10 |
| Total tablet mass | 130.00 |

Formulation Example 7

A hard gelatin capsule, comprising as active ingredient e.g. (S)—N-(1-carboxy-2-methylprop-1-yl)-N-pentanoyl-N-[2' (1H-tetrazol-5-yl)biphenyl-4-yl-methyl]amine, can be formulated, for example, as follows:
Composition:

| | |
|---|---|
| (1) valsartan | 80.0 mg |
| (2) microcrystalline cellulose | 110.0 mg |
| (3) polyvidone K30 | 45.2 mg |
| (4) sodium lauryl sulfate | 1.2 mg |
| (5) crospovidone | 26.0 mg |
| (6) magnesium stearate | 2.6 mg |

Components (1) and (2) are granulated with a solution of components (3) and (4) in water. The components (5) and (6) are added to the dry granulate and the mixture is filled into size 1 hard gelatin capsules.

All publications and patents mentioned herein are incorporate by reference in their entirety as if set forth in full herein.

What is claimed is:

1. A pharmaceutical composition comprising:
   (i) the AT 1-antagonist valsartan or a pharmaceutically acceptable salt thereof;
   (ii) the NEP inhibitor N-(3-carboxy-1-oxopropyl)-(4S)-(p-phenylphenylmethyl)-4-amino-2R-methylbutanoic acid ethyl ester or a pharmaceutically acceptable salt thereof, or (2R,4S)-5-biphenyl-4-yl-4(3-carboxy-propionyl amino)-2-methyl-pentanoic acid or a pharmaceutically acceptable salt thereof; and
   (iii) a pharmaceutically acceptable carrier;
   wherein said (i) AT 1-antagonist valsartan or a pharmaceutically acceptable salt thereof and said (ii) NEP inhibitor N-(3-carboxy-1-oxopropyl)-(4S)-(p-phenylphenylmethyl)-4-amino-2R-methylbutanoic acid ethyl ester or a pharmaceutically acceptable salt thereof, or (2R,4S)-5-biphenyl-4-yl-4(3-carboxy-propionyl amino)-2-methyl-pentanoic acid or a pharmaceutically acceptable salt thereof, are administered in combination in a 1:1 ratio.

2. The pharmaceutical composition of claim 1 wherein (ii) said NEP inhibitor is N-(3-carboxy-1-oxopropyl)-(4S)-(p-phenylphenylmethyl)-4-amino-2R-methylbutanoic acid ethyl ester.

3. The pharmaceutical composition of claim 1 wherein (ii) said NEP inhibitor is a pharmaceutically acceptable salt of N-(3-carboxy-1-oxopropyl)-(4S)-(p-phenylphenylmethyl)-4-amino-2R-methylbutanoic acid ethyl ester.

4. The pharmaceutical composition of claim 1 wherein (ii) said NEP inhibitor is (2R,4S)-5-biphenyl-4-yl-4(3-carboxy-propionyl amino)-2-methyl-pentanoic acid.

5. The pharmaceutical composition of claim 1 wherein (ii) said NEP inhibitor is a pharmaceutically acceptable salt of (2R,4S)-5-biphenyl-4-yl-4(3-carboxy-propionyl amino)-2-methyl-pentanoic acid.

6. A pharmaceutical composition comprising:
   (i) the AT 1-antagonist valsartan or a pharmaceutically acceptable salt thereof;
   (ii) the NEP inhibitor N-(3-carboxy-1-oxopropyl)-(4S)-(p-phenylphenylmethyl)-4-amino-2R-methylbutanoic acid ethyl ester or a pharmaceutically acceptable salt thereof, or (2R,4S)-5-biphenyl-4-yl-4(3-carboxy-propionyl amino)-2-methyl-pentanoic acid or a pharmaceutically acceptable salt thereof; and
   (iii) a pharmaceutically acceptable carrier;
   wherein said (i) AT 1-antagonist valsartan or a pharmaceutically acceptable salt thereof and said (ii) NEP inhibitor N-(3-carboxy-1-oxopropyl)-(4S)-(p-phenylphenylmethyl)-4-amino-2R-methylbutanoic acid ethyl ester or a pharmaceutically acceptable salt thereof, or (2R,4S)-5-biphenyl-4-yl-4(3-carboxy-propionyl amino)-2-methyl-pentanoic acid or a pharmaceutically acceptable salt thereof, are present in a 1:1 ratio.

7. A pharmaceutical composition consisting of:
   (i) the AT 1-antagonist valsartan or a pharmaceutically acceptable salt thereof;
   (ii) the NEP inhibitor N-(3-carboxy-1-oxopropyl)-(4S)-(p-phenylphenylmethyl)-4-amino-2R-methylbutanoic acid ethyl ester or a pharmaceutically acceptable salt thereof, or (2R,4S)-5-biphenyl-4-yl-4(3-carboxy-propionyl amino)-2-methyl-pentanoic acid or a pharmaceutically acceptable salt thereof; and
   (iii) a pharmaceutically acceptable carrier;
   wherein said (i) AT 1-antagonist valsartan or a pharmaceutically acceptable salt thereof and said (ii) NEP inhibitor N-(3-carboxy-1-oxopropyl)-(4S)-(p-phenylphenylmethyl)-4-amino-2R-methylbutanoic acid ethyl ester or a pharmaceutically acceptable salt thereof, or (2R,4S)-5-biphenyl-4-yl-4(3-carboxy-propionyl amino)-2-methyl-pentanoic acid or a pharmaceutically acceptable salt thereof, are present in a 1:1 ratio.

8. The pharmaceutical composition of claim 3 wherein the pharmaceutically acceptable salt is selected from the group consisting of the sodium salt, the triethanolamine salt and the tris(hydroxymethyl)aminomethane salt.

9. The pharmaceutical composition of claim 5 wherein the pharmaceutically acceptable salt is selected from the group consisting of the sodium salt, the triethanolamine salt and the tris(hydroxymethyl)aminomethane salt.

10. The pharmaceutical composition of claim 1 in the form of a capsule or tablet.

* * * * *